(12) United States Patent
Ridler

(10) Patent No.: US 9,248,287 B2
(45) Date of Patent: Feb. 2, 2016

(54) SOUND PROCESSOR ACCESSORY

(71) Applicant: Oliver Ridler, Sydney (AU)

(72) Inventor: Oliver Ridler, Sydney (AU)

(73) Assignee: Cochlear Limited, Macquarie University, NSW (AU)

( * ) Notice: Subject to any disclaimer, the term of this patent is extended or adjusted under 35 U.S.C. 154(b) by 141 days.

(21) Appl. No.: 13/919,226

(22) Filed: Jun. 17, 2013

(65) Prior Publication Data
US 2014/0371815 A1    Dec. 18, 2014

(51) Int. Cl.
H04R 25/00 (2006.01)
A61N 1/36 (2006.01)
A61N 1/05 (2006.01)

(52) U.S. Cl.
CPC .......... *A61N 1/36032* (2013.01); *A61N 1/0541* (2013.01); *H04R 25/43* (2013.01); *H04R 25/554* (2013.01); *H04R 2225/021* (2013.01); *H04R 2225/67* (2013.01)

(58) Field of Classification Search
USPC .......................................................... 381/331
See application file for complete search history.

(56) References Cited

U.S. PATENT DOCUMENTS

| 7,020,298 | B1 | 3/2006 | Tziviskos et al. | |
| 7,054,691 | B1 | 5/2006 | Kuzma et al. | |
| 7,142,926 | B2 | 11/2006 | Crawford | |
| 7,369,671 | B2* | 5/2008 | Sacha | H04R 25/43 381/312 |
| 7,869,883 | B2 | 1/2011 | Seligman | |
| 8,139,802 | B2* | 3/2012 | Lotter et al. | 381/331 |
| 2001/0055404 | A1* | 12/2001 | Bisgaard | 381/314 |
| 2008/0292124 | A1* | 11/2008 | Rosenow et al. | 381/322 |
| 2011/0116669 | A1 | 5/2011 | Karunasiri | |

* cited by examiner

*Primary Examiner* — Davetta W Goins
*Assistant Examiner* — Amir Etesam
(74) *Attorney, Agent, or Firm* — Edell, Shapiro & Finnan, LLC

(57) ABSTRACT

Embodiments presented herein are generally directed to a sound processor accessory configured to be mechanically and electrically connected to a sound processor of an auditory prosthesis. The sound processor accessory comprises first and second sound input elements that are each configured to independently provide electrical signals representing sound signals to the sound processor via a shared connection.

27 Claims, 9 Drawing Sheets

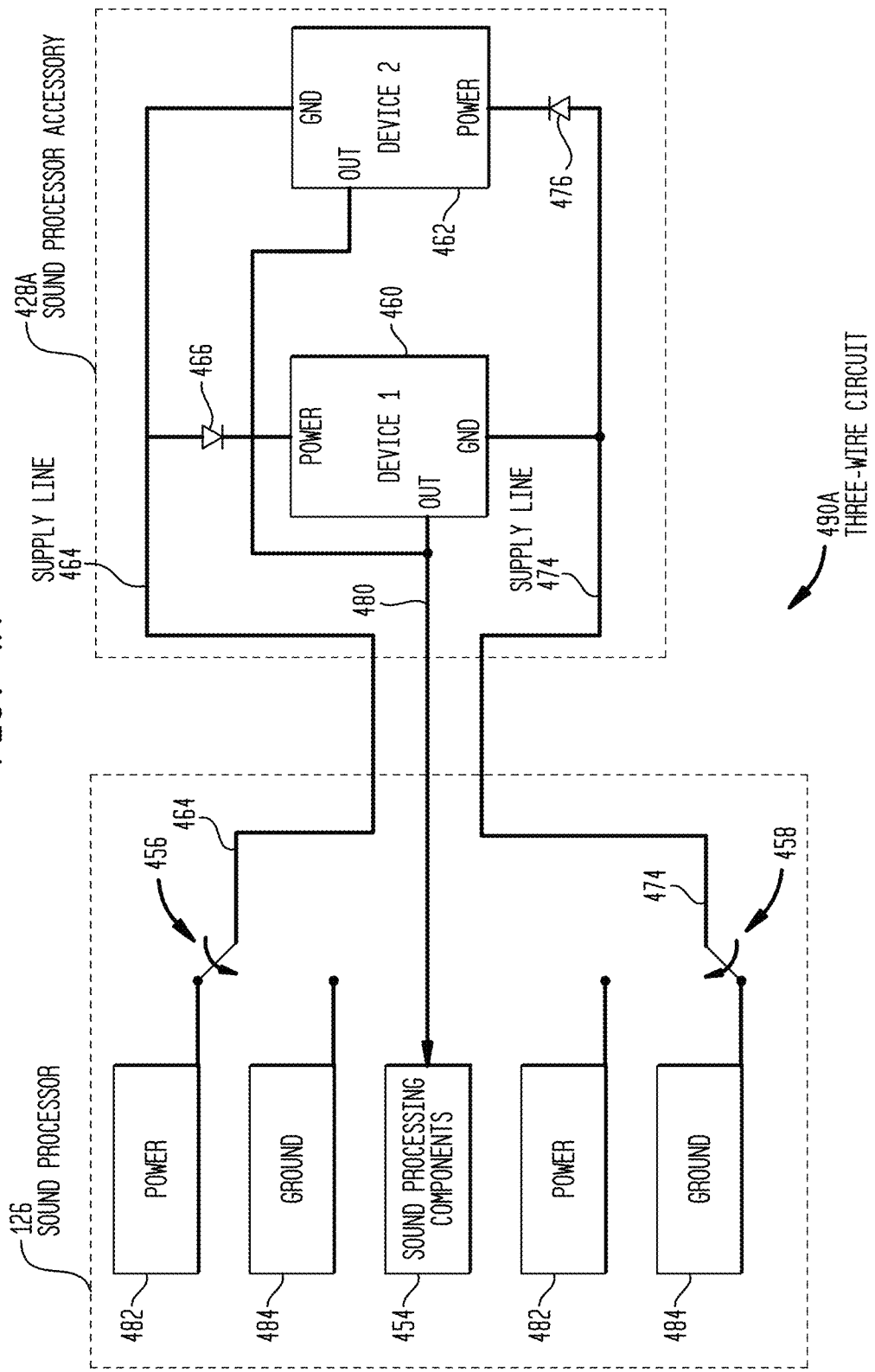

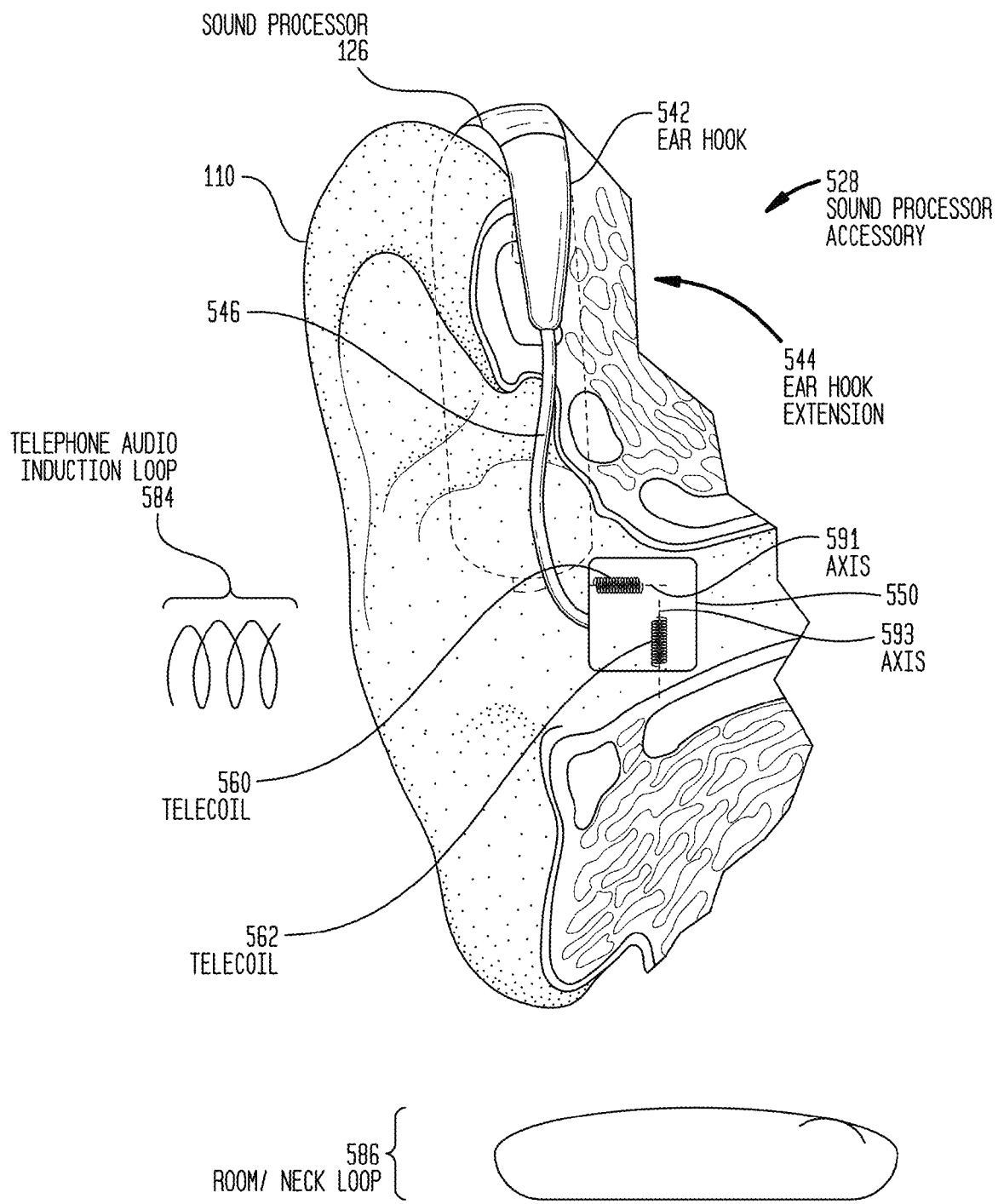

SOUND PROCESSOR ACCESSORY

BACKGROUND

1. Field of the Invention

The present invention relates generally to a sound processor for an auditory prosthesis, and more particularly, to a sound processor accessory.

2. Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

Many auditory prostheses include and/or operate in conjunction with an external sound processor. When in use, these sound processors are worn by, or otherwise secured to, the recipient.

SUMMARY

In one aspect, a sound processor accessory is provided. The sound processor accessory comprises first and second sound input elements, and a shared connection configured to electrically connect the first and second sound input elements to sound processing components of a sound processor such that first and second sound input elements independently provide electrical signals to the sound processing components.

In another aspect, an apparatus is provided. The apparatus comprises a first three-wire device, a second three-wire device, and a three-wire connection configured to selectably enable one or the other of the first and second three-wire devices for operation with connected sound processing components of a sound processor.

In a further aspect, an apparatus is provided. The apparatus comprises a first set of one or more devices, a second set of one or more devices, and a circuit connecting both of the first and second sets of one or more devices to components of a sound processor such that the first and second sets of one or more devices are alternatively operable.

In another aspect, an auditory prosthesis is provided. The auditory prosthesis comprises a sound processor and a separate sound processor accessory electrically connected to the sound processor and comprising one or more telecoils. The one or more telecoils are the only telecoils present in the auditory prosthesis.

BRIEF DESCRIPTION OF THE DRAWINGS

Embodiments are described herein in conjunction with the accompanying drawings, in which:

FIG. 4A is a schematic circuit diagram of a sound processor and sound processor accessory in accordance with embodiments presented herein;

FIG. 5 is a schematic diagram of a sound processor accessory comprising first and second telecoils in accordance with embodiments presented herein.

DETAILED DESCRIPTION

Embodiments presented herein are generally directed to a sound processor accessory configured to be mechanically and electrically connected to a sound processor of an auditory prosthesis. The sound processor accessory comprises first and second sound input elements that are each configured to independently provide electrical signals representing sound signals to the sound processor via a shared connection.

For ease of illustration, embodiments are primarily described herein with reference to a sound processor and sound processor accessory used with a cochlear implant (also commonly referred to as cochlear implant device, cochlear prosthesis, and the like; simply "cochlear implant" herein). However, it is to be appreciated that embodiments may be used in conjunction with different sound processors and sound processor accessories for other auditory prostheses (e.g., bone conduction devices, auditory brain stimulators, mechanical stimulators, etc.).

Figure 1:
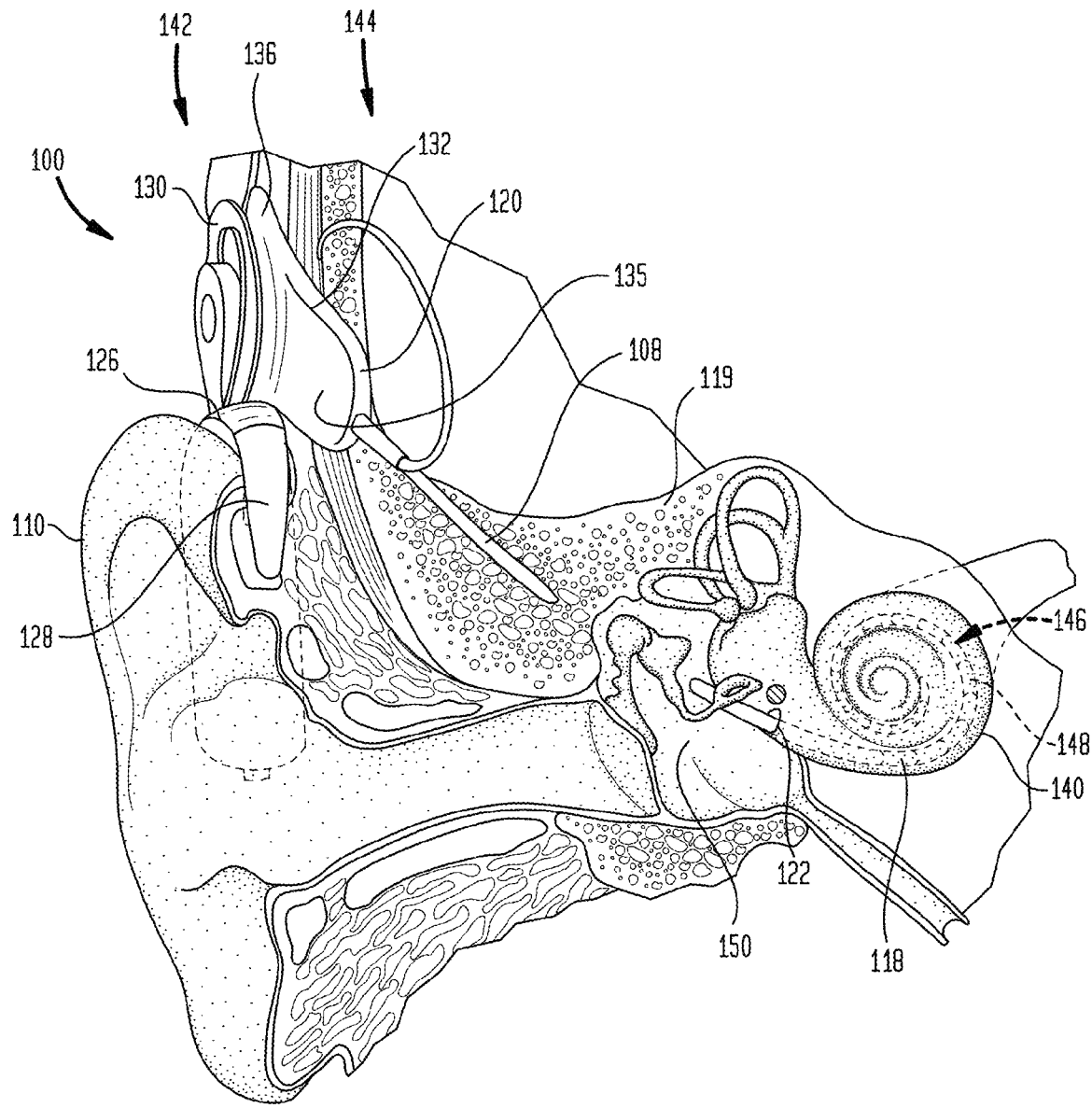
FIG. 1 is a schematic diagram of one embodiment of an exemplary auditory prosthesis in accordance with embodiments presented herein.

FIG. 1 is perspective view of an exemplary cochlear implant 100 in which embodiments presented herein may be implemented. The cochlear implant 100 comprises an external component 142 and an internal or implantable component 144. The external component 142 comprises a sound processing unit (sound processor) 126 and a sound processor accessory 128. The sound processor 126 and/or sound processor accessory 128 are configured to be directly or indirectly attached to the body of the recipient.

The sound processor accessory 128 comprises a plurality of sound input elements (not shown) and is configured to mechanically and electrically connect to the sound processor 126. The sound input elements may comprise, for example, microphones, telecoils, etc. The external component 142 also comprises a power source (in sound processor 126), an external coil 130 and, generally, a magnet (not shown) fixed relative to the external coil 130. The sound processor 126 includes one or more hardware and/or software components configured to process electrical signals received from the sound input elements. The sound processor 126 provides the processed signals to external coil 130 via a cable (not shown).

The internal component 144 comprises an elongate stimulating assembly 118, a stimulator unit 120, and an internal receiver/transceiver unit 132, sometimes referred to herein as transceiver unit 132. The transceiver unit 132 is connected to an internal coil 136 and, generally, a magnet (not shown) fixed relative to the internal coil 136.

The magnets in the external component 142 and internal component 144 facilitate the operational alignment of the external coil 130 with the internal coil 136. The operational alignment of the coils enables the internal coil 136 to transmit/receive power and data to/from the external coil 130. More specifically, in certain examples, external coil 130 transmits electrical signals (e.g., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding. In use, transceiver unit 132 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 is implanted in cochlea 140 and includes a contact array 146 comprising a plurality of stimulating contacts 148. Stimulating assembly 118 extends through cochleostomy 122 and has a proximal end connected to stimulator unit 120 via lead region 108 that extends through mastoid bone 119.

Internal transceiver unit 132 and stimulator unit 120 are disposed in a hermetically-sealed and biocompatible housing 135. The housing 135 operates as a protective barrier between the electrical components (e.g., in transceiver unit 132 and stimulator unit 120) and the recipient's tissue and bodily fluid. Prior to implantation, the housing 135 and the internal coil 136 may be overmolded or coated with a silicone elastomer to create a uniform compliant surface suitable for implantation.

Figure 2:
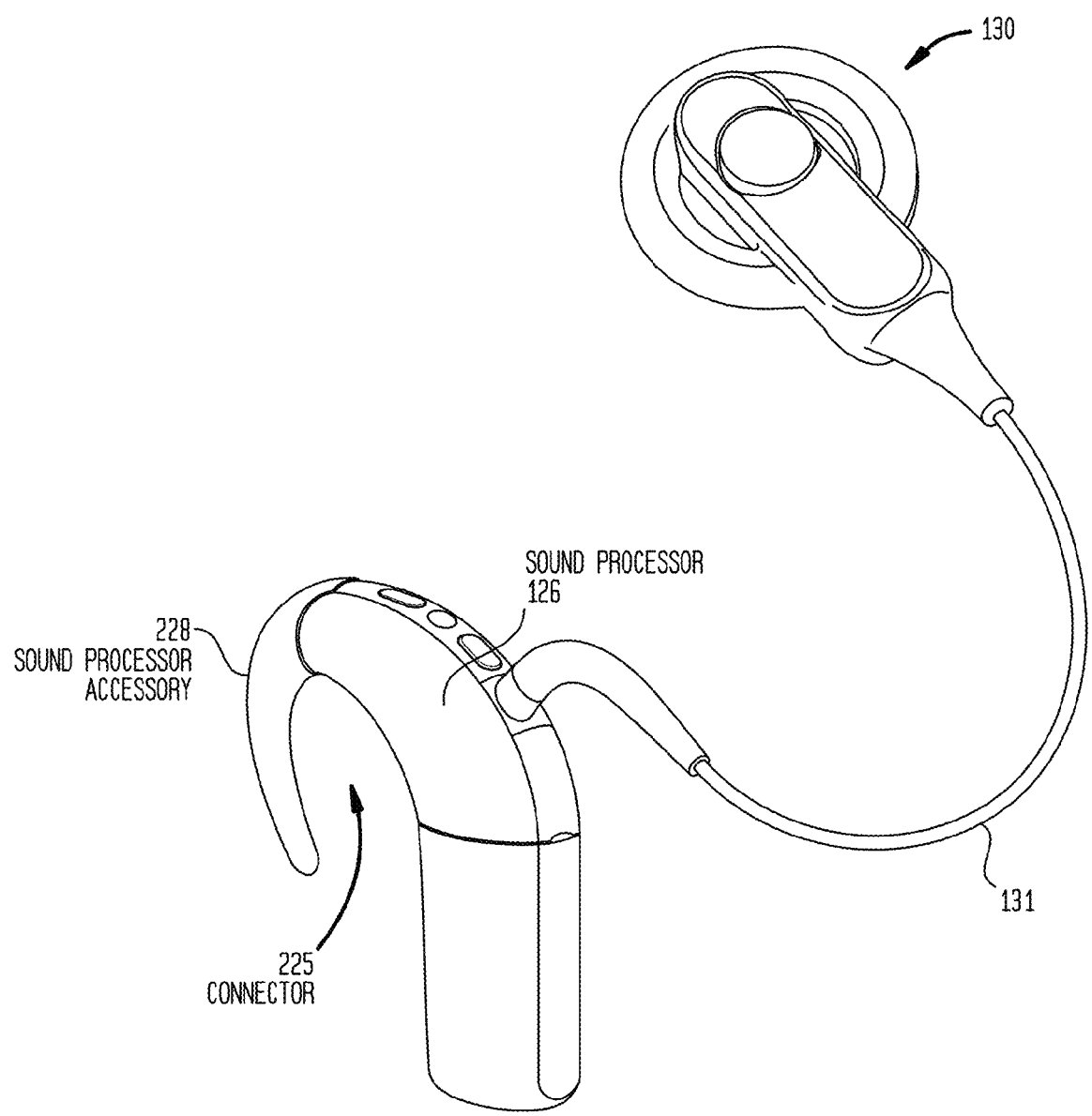
FIG. 2 is a side view of an external component of an auditory prosthesis in accordance with embodiments presented herein.

FIG. 2 is a side view of one embodiment of external component 142 of FIG. 1. In the embodiment of FIG. 2, the external component 142 comprises sound processor 126 attached to external coil 130 via a cable 131. The sound processor 126 is also attached to one embodiment of sound processor accessory 128 of FIG. 1, referred to in FIG. 2 as sound processor accessory 228.

In the embodiment of FIG. 2, the sound processor 126 is a behind-the-ear sound processor and the sound processor accessory 228 is an ear hook. That is, the sound processor accessory 228 is configured to detachably mate with the front of sound processor 126 and has a generally curved shape forming a mechanism by which the sound processor may hang from the recipient's ear. The sound processor accessory 228 is configured to mechanically mate with the sound processor 126, and is electrically connected to the sound processor via a three-wire connector 225. The connector 225 may be, for example, a three contact plug and socket arrangement.

The plug is a male plastic member of the sound processor accessory 228 that mates with a female plastic socket in the sound processor 126. The male plastic plug contains three female electrical receptacles that accept three male pins inside the female socket in the sound processor 126. A latch (not shown) may be operated to remove the plug from the socket.

The sound processor accessory 228 comprises a plurality of sound input elements (not shown), such as microphones, telecoils, audio input ports, etc., that are configured to detect/receive sound signals. The plurality of sound input elements in the sound processor accessory 228 are electrically connected to sound processing components in the sound processor 126. As described below, the electrical connection between the sound input elements and the sound processing components is such that the sound input elements are selectively operable so as to independently provide electrical signals representative of the received sound signals to the sound processing components in sound processor 126.

Figure 3:
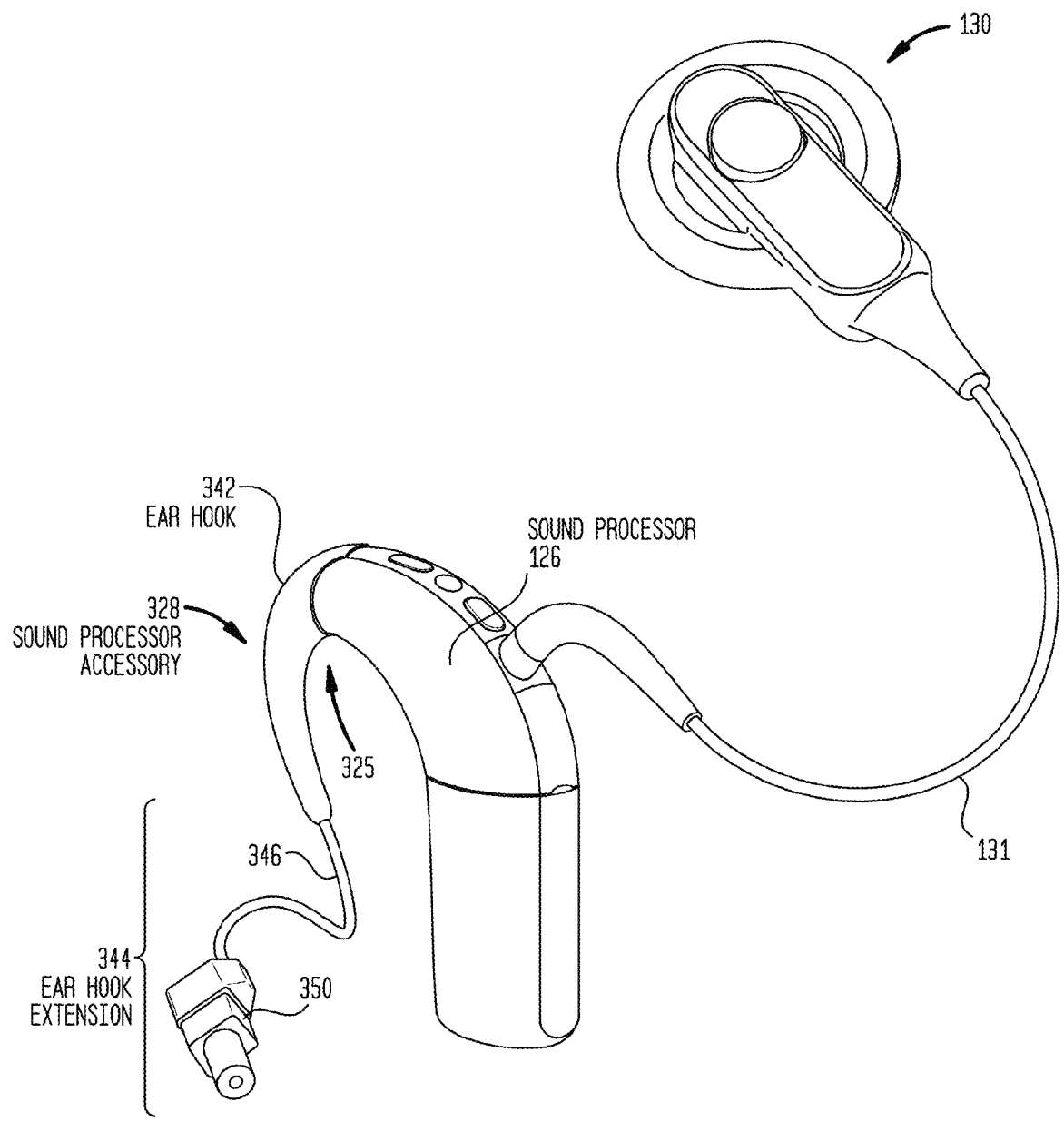
FIG. 3 is a side view of another external component of an auditory prosthesis in accordance with embodiments presented herein.

FIG. 3 is a side view of another embodiment of external component 142 of FIG. 1. In the embodiment of FIG. 3, the external component 142 comprises sound processor 126 attached to external coil 130 via a cable 131. The sound processor 126 is also attached to another embodiment of sound processor accessory 128 of FIG. 1, referred to in FIG. 3 as sound processor accessory 328. In the embodiment of FIG. 3, the sound processor 126 is a behind-the-ear sound processor and the sound processor accessory 328 comprises two main elements, namely an ear hook 342 and an ear hook extension 344. The ear hook extension 344 comprises a shaft 346 extending from the ear hook 342 and a near-the-canal component 350. The sound processor accessory 328 is configured to mechanically mate with the sound processor 126, and is electrically connected to the sound processor via a connector 325 that is similar to the connector 225 of FIG. 2.

Similar to sound processor accessory 228 of FIG. 2, the sound processor accessory 328 comprises a plurality of sound input elements (not shown), such as microphones, telecoils, audio input ports, etc., that are configured to detect/receive sound signals. The plurality of sound input elements in the sound processor accessory 328 are electrically connected to sound processing components in the sound processor 126. As described below, the electrical connection between the sound input elements and the sound processing components is such that the sound input elements are selectively operable so as to independent provide electrical signals representative of the received sound signals to the sound processing components in sound processor 126.

It is to be appreciated that the sound processor and sound processor accessories shown in FIGS. 2 and 3 are merely illustrative and that other variations are possible. For example, sound processor accessories in accordance with embodiments presented herein may be used with button processors, body worn processors, etc. For each of these different variations, the sound processor accessories will include multiple sound input elements, but may have different physical configurations (i.e., different shapes, sizes, etc.).

As noted above, a sound processor accessory in accordance with embodiments presented herein, such as sound processor accessories 228 and 328, include a plurality (i.e., two or more) of sound input elements. In certain embodiments, a sound processor accessory includes two sound input elements that are selectably connected to sound processing components of a sound processor via a three-wire connection, sometimes referred to herein as a three-wire circuit. FIGS. 4A-4D are schematic diagrams illustrating the use of a three-wire connection to connect two sound input elements disposed in a sound processor accessory to sound processing components in a sound processor.

As noted above, sound processor accessories in accordance with embodiments presented herein may be detachably connected to a sound processor. As such, mechanical and electrical connector(s) (which may be separate connectors or an integrated connector) may be provided to attach a sound processor accessory to a sound processor. Merely for ease of illustration, the mechanical and electrical connector(s) are omitted from FIGS. 4A-4D.

FIG. 4A schematically illustrates that sound processor 126 comprises one or more sound processing components 454, a first switch 456, and a second switch 458. FIG. 4A also schematically illustrates a sound processor accessory 428A that comprises a first sound input element 460 (device 1) and a second sound input element 462 (device 2). The sound processor accessory 428A may be an ear hook (such as shown in FIG. 2) or an ear hook with an ear hook extension that includes, for example, a near-the-canal component, an in-the-canal component, etc.

The sound input elements 460 and 462 are both three-wire devices, sometimes referred to as three-terminal or three-pin devices. That is, each of the sound input elements 460 and 462 include a ground terminal (GND), a power terminal (POWER), and a signal connection or output terminal (OUT).

The first switch 456 (connected to supply line 464) and the second switch 458 (connected to supply line 474) are each selectably and alternatively connectable to a power source (power) 482 and a ground 484 in sound processor. While first switch 456 is connected to the power source 482 (i.e., connecting supply line 464 to power), the second switch 458 is connected to the ground 484 (i.e., connecting supply line 474 to ground). This arrangement of the switches 456 and 458 is referred to herein as a first configuration of the three-wire connection 490A and results in the powering of the first sound input element 460. Conversely, while first switch 456 is connected to the ground 484 (i.e., connecting supply line 464 to ground), the second switch 458 is connected to the power 482 (i.e., connecting supply line 474 to power). This arrangement of the switches 456 and 458 is referred to herein as a second configuration of the three-wire connection 490A and results in the powering of the second sound input element 462.

As shown, the cathode of diode 466 is connected to the POWER terminal of sound input element 460, while the anode of diode 466 is connected to supply line 464. Therefore, diode 466 only permits current to flow when it is forward biased with supply line 464 connected to (positive) power 482, which is at a higher potential than supply line 474 which is connected to ground 484. Alternatively, when supply line 464 is connected to ground 484 and supply line 474 is connected to power 482, supply line 464 is at a more negative potential than supply line 474 and so diode 466 is reverse biased and substantially prevents current flow.

Additionally, the cathode of diode 476 is connected to the POWER terminal of sound input element 462, while the anode of diode 476 is connected to supply line 474. Therefore, diode 476 only permits current to flow when it is forward biased with supply line 474 connected to (positive) power 482, which is at a higher potential than supply line 464 which is connected to ground 484. Alternatively, when supply line 474 is connected to ground 484 and supply line 464 is connected to power 482, supply line 474 is at a more negative potential than supply line 464 and so diode 476 is reverse biased and substantially prevents current flow.

The output terminals of both the first sound input element 460 and the second sound input element 462 are connected to a signal line 480. The signal line 480 is also connected to the sound processing components 454 in the sound processor 126. The switches 456 and 458, the supply lines 464 and 474, the diodes 466 and 476, and the signal line 480 collectively form a three-wire connection (three-wire circuit) 490A.

As shown, the output terminals, and thus output signals (i.e., signals representative of received sound signals) from the first and sound input elements 460 and 462 are connected together at signal line 480. However, at any time, only one of the first and second sound input elements is powered, while the other one is unpowered. In the embodiment of FIG. 4A, the unpowered sound input element does not interfere with the active sound input element because the unpowered device puts its output into a high impedance state.

In summary, in the embodiment of FIG. 4A, the first sound input element 460 and the second input element 462 are alternatively operable, depending on the configuration of the three-wire connection 490A. In other words, the three-wire connection 490A is configured to selectably enable one or the other of the first and second sound input elements for operation with the connected sound processing components 454.

Certain conventional arrangements use two audio sources positioned externally to a sound processor. In such arrangements, mixer circuits are used to combine input signals from the two sources so that both of the signals can be transmitted together (i.e., simultaneously in a mixed form) for subsequent processing. These conventional arrangements have several disadvantages. A primary disadvantage is the requirement of complex circuitry (i.e., mixing circuit) in order to combine sounds from two sources. Additionally, due to the nature of the conventional solutions (i.e., the use of a mixing circuit that requires the signals to be combined before transmission), these conventional arrangements do not work with arrangements in which signals from two of the same type of audio sources (e.g., two microphones, two telecoils, etc.) are combined (i.e., the signals from two of the same type of devices, when combined, would be indistinguishable).

Embodiments presented herein do not suffer from the same constraints as these conventional arrangements and are usable with two of the same sound input elements. Another advantage of embodiments presented here is the use of only three wires and thus only three pins in a connector between a sound processor accessory and a sound processor. The use of more pins/wires results in a larger connector, thus embodiments presented herein enable the use of a connector that is smaller than arrangements that use four or more wires (i.e., by not increasing the number of pins to four, the size of the connector does not need to be increased).

As noted, the three-wire connection 490A independently connects the two sound input elements 460 and 462 to the sound processing components 454 (i.e., no mixing). This independent connection has the benefit over conventional arrangements in that it enables the use of a variety of different combination of sound input elements. In particular, the independent connection provided by the three-wire circuit 490A enables the use of two of the same type of sound input elements or two different types of sound input elements in the sound processor accessory 428A. For example, in certain embodiments, the first and second sound input elements 460 and 462 may each be a telecoil. In alternative embodiments, the first and second sound input elements 460 and 462 may each be a microphone. In still other embodiments, the first sound input element 460 may be a microphone while the second sound input element 462 may be a telecoil. In further embodiments, one or both of the sound input elements may be an audio input port.

Figure 4B:
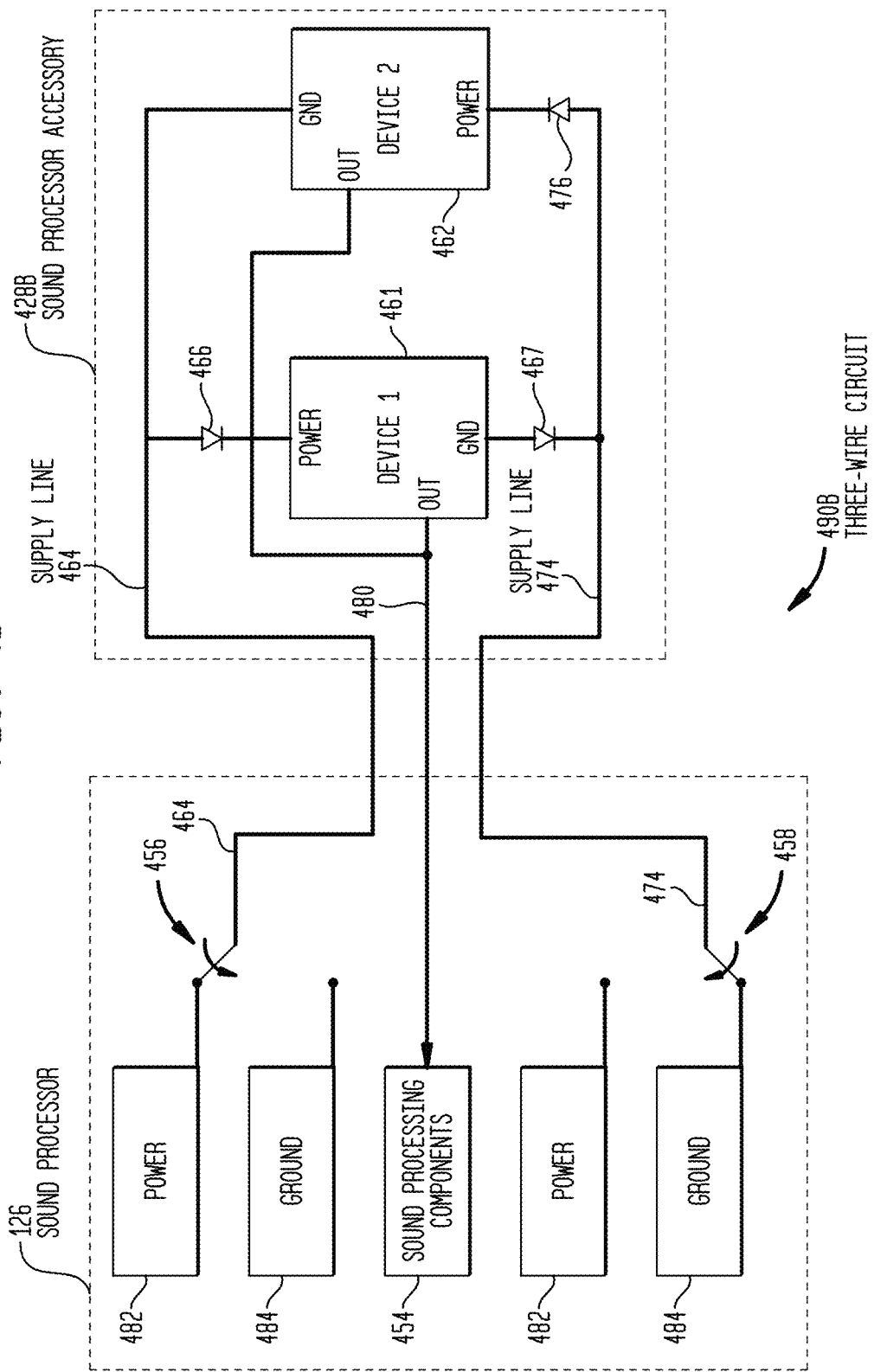
FIG. 4B is a schematic circuit diagram of a sound processor and sound processor accessory in accordance with embodiments presented herein.

As shown, FIG. 4A illustrates the use of two diodes (diodes 466 and 476) in the three-wire connection 490A. This two diode arrangement is effective when used with sound input elements that have output terminals that have high impedance when the device is not powered (unpowered). If sound input elements are used that include output terminals that have low impedance when inactive, then the three-wire circuit may include additional diodes to effectively isolate the unpowered device. For example, FIG. 4B illustrates an alternative sound processor accessory 428B configured to be connected to sound processor 126 via a three-wire circuit (three-wire connection) 490B. Sound processor accessory 428B is substantially similar to sound processor accessory 428A of FIG. 4A, except that it includes a first sound input element 461 and a second sound input element 462 (as described above). The first sound input element 461 is, in this example, a three-wire device having an output terminal that is low-impedance when the sound input element 461 is unpowered.

The first switch 456 (connected to supply line 464) and the second switch 458 (connected to supply line 474) are each selectably and alternatively connectable to power 482 and ground 484 in the sound processor 126. More specifically, while first switch 456 is connected to the power source 482 (i.e., connecting supply line 464 to power), the second switch 458 is connected to the ground 484 (i.e., connecting supply line 474 to ground). This arrangement of the switches 456 and 458 is referred to herein as a first configuration of the three-wire circuit 490B and results in the powering of the first sound input element 461. Conversely, while first switch 456 is connected to the ground 484 (i.e., connecting supply line 464 to ground), the second switch 458 is connected to the power source 484 (i.e., connecting supply line 474 to power). This arrangement of the switches 456 and 458 is referred to herein as a second configuration of the three-wire circuit 490B and results in the powering of the second sound input element 462.

Three-wire circuit 490B is substantially similar to the three-wire circuit 490A of FIG. 4A, except that it includes an additional diode 467. More specifically, the first switch 456 is connected to supply line 464 that extends to the GND terminal of the second sound input element 462 and to the diode 466 connected to the POWER terminal of the first sound input element 461. Diodes 466 and 467 have anode and cathode connections such that the power terminal of the first sound input element 461 is effectively connected to the supply line 464 and the ground terminal of 461 is connected to supply line 474 when the supply line 464 is at a higher potential than supply 474 (i.e., supply line 464 is connected to power 482 and supply line 474 is connected to ground 484). Similarly, the power terminal of first sound input element 461 is largely disconnected from supply line 464 when diode 466 is reverse biased and the ground terminal for 461 is disconnected from supply line 474 when diodes 466 and 467 are reverse biased by having supply line 464 at a lower potential than supply line 474 (i.e., supply line 464 is connected to ground 484 and supply line 474 is connected to power 482).

The output terminals of both the first sound input element 461 and the second sound input element 462 are connected to a signal line 480. The signal line 480 is also connected to the sound processing components 454 in the sound processor 126. The switches 456 and 458, the supply lines 464 and 474, the diodes 466, 476, and 467, and the signal line 480 collectively form a three-wire circuit (three-wire connection) 490B.

In summary, in the embodiment of FIG. 4B the first sound input element 461 and the second input element 462 are alternatively operable, depending on the configuration of the three-wire connection 490B. In other words, the shared three-wire circuit 490B is configured to selectably enable one or the other of the first and second sound input elements for operation with the connected sound processing components 454.

In the embodiment of FIG. 4B, the second sound input element 462 has an output terminal that goes into a high impedance state when unpowered, thus a second diode is not required at this GND terminal because its output will not interfere with the first sound input element 461. However, an output terminal of the first sound input element 461 is not required to go into any particular state because the attached diode 467 ensures that its output will not interfere with the second sound input element 462.

Figure 4C:
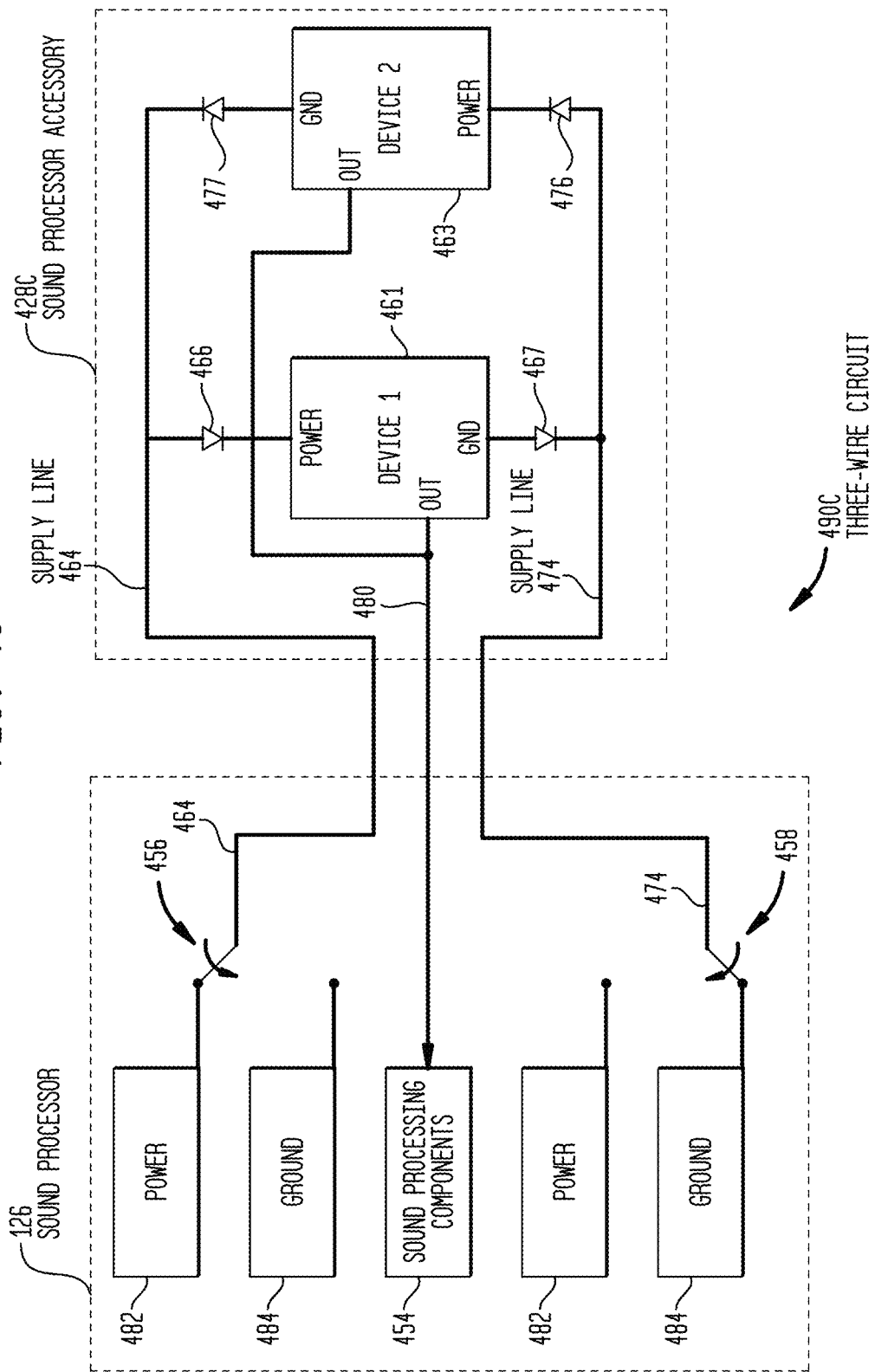
FIG. 4C is a schematic circuit diagram of a sound processor and sound processor accessory in accordance with embodiments presented herein.

FIG. 4C illustrates an alternative sound processor accessory 428C configured to be connected to sound processor 126 via a three-wire circuit (three-wire connection) 490C. Sound processor accessory 428C is substantially similar to sound processor accessory 428A of FIG. 4A, except that it includes a first sound input element 461 (as described above) and a second sound input element 463. The first and second sound input elements 461 and 463 are, in this example, three-wire devices having output terminals that are low-impedance when the sound input elements 461 and 462 are inactive.

The first switch 456 (connected to supply line 464) and the second switch 458 (connected to supply line 474) are each selectably and alternatively connectable to a power source (power) 482 and a ground 484 in sound processor. More specifically, while first switch 456 is connected to the power source 482 (i.e., connecting supply line 464 to power), the second switch 458 is connected to the ground 484 (i.e., connecting supply line 474 to ground). This arrangement of the switches 456 and 458 is referred to herein as a first configuration of the three-wire circuit 490C and results in the powering of the first sound input element 461. Conversely, while first switch 456 is connected to the ground 484 (i.e., connecting supply line 464 to ground), the second switch 458 is connected to the power source 484 (i.e., connecting supply line 474 to power). This arrangement of the switches 456 and 458 is referred to herein as a second configuration of the three-wire circuit 490C and results in the powering of the second sound input element 463.

Three-wire circuit 490C is substantially similar to three-wire circuit 490B of FIG. 4B, except that it includes an additional diode 477. Diodes 476 and 477 have anode and cathode connections such that the power terminal of the second sound input element 463 is effectively connected to the supply line 474 and the ground terminal of 463 is connected to supply line 464 when the supply line 474 is at a higher potential than supply 464 (i.e., supply line 474 is connected to power 482 and supply line 464 is connected to ground 484). Similarly, the power terminal of the second sound input element 463 is largely disconnected from supply line 474 and the ground terminal of 463 is disconnected from supply line 464 when diode 476 is reverse biased by having supply line 474 at a lower potential than supply line 464 (i.e., supply line 474 is connected to ground 484 and supply line 464 is connected to power 482).

The output terminals of both the first sound input element 461 and the second sound input element 463 are connected to a signal line 480. The signal line 480 is also connected to the sound processing components 454 in the sound processor 126. The switches 456 and 458, the supply lines 464 and 474, the diodes 466, 476, 467, and 477, and the signal line 480 collectively form a three-wire circuit (three-wire connection) 490C.

In summary, in the embodiment of FIG. 4C, the first sound input element 461 and the second input element 463 are alternatively operable, depending on the configuration of the shared three-wire circuit 490C. In other words, the shared three-wire circuit 490C is configured to selectably enable one or the other of the first and second sound input elements for operation with the connected sound processing components 454.

Figure 4D:
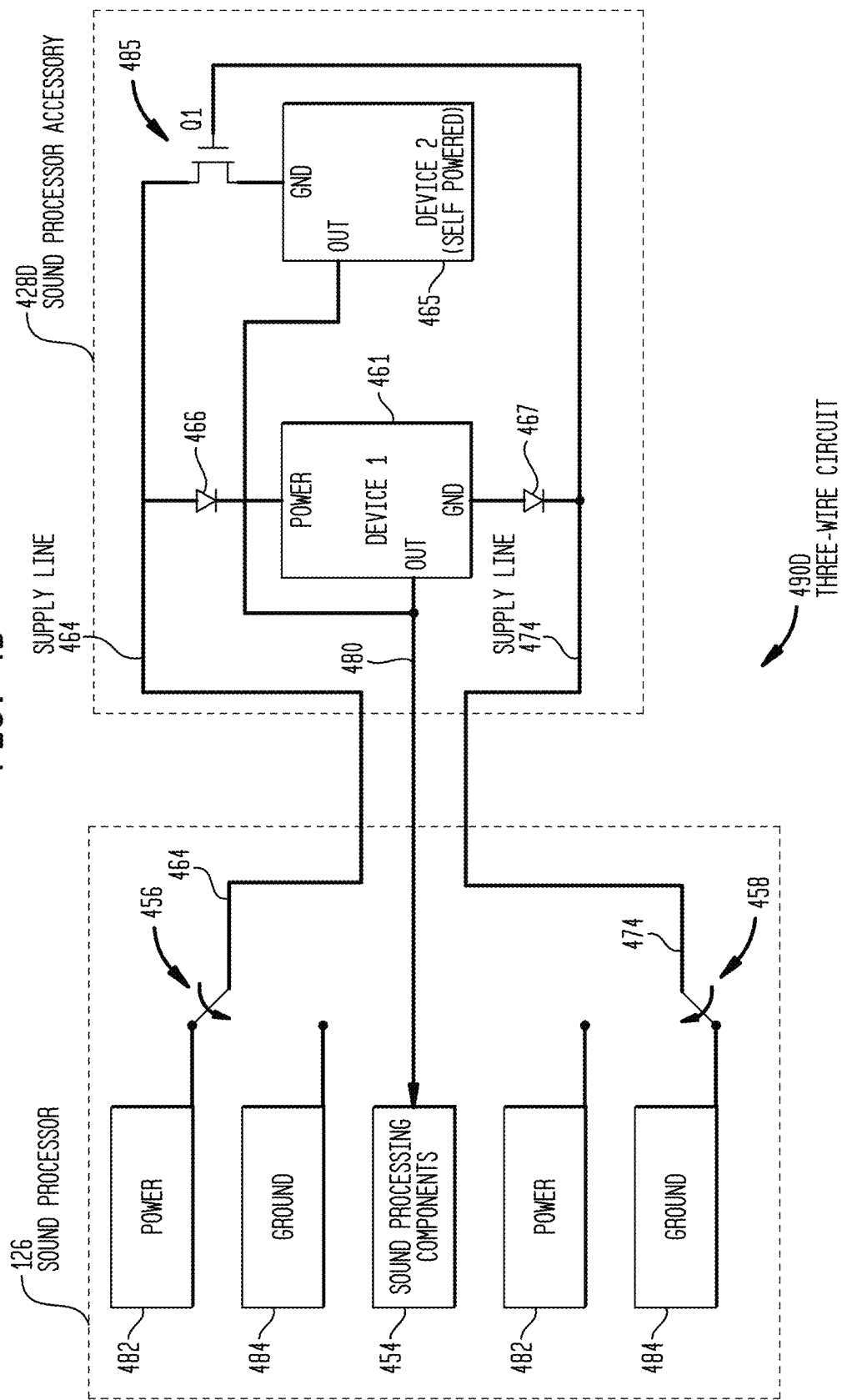
FIG. 4D is a schematic circuit diagram of a sound processor and sound processor accessory in accordance with embodiments presented herein.

FIG. 4D illustrates another sound processor accessory 428D configured to be connected to sound processor 126 via a three-wire circuit (three-wire connection) 490D. Sound processor accessory 428D includes a first sound input element 461 (as described above) and a second sound input element 465. In the embodiment of FIG. 4D, the first sound input element 461 is a three-wire device having an output terminal that is low-impedance when the sound input element 461 is inactive. In contrast, sound input element 465 is a two-terminal, self-powered device. Sound input element 465 is, for example, an audio input port for connection to an external audio source (e.g., computer, television, mobile phone, radio, iPod®, FM receiver, etc.).

Three-wire circuit 490D includes supply lines 464 and 474 and diodes 466 and 477 as described above. The first switch 456 is connected to supply line 464 that extends to a diode 466 connected to the POWER terminal of the first sound input element 461. The supply line 464 is also directly connected to a first terminal (i.e., the drain) of a transistor 485. The transistor 485 has a second terminal (i.e., the source) connected to the GND terminal of the second sound input element 465. The supply line 474 is also connected to the third terminal (i.e., the gate) of the transistor 485.

The output terminals of both the first sound input element 461 and the second sound input element 465 are connected to a signal line 480. The signal line 480 is also connected to the sound processing components 454 in the sound processor 126. The switches 456 and 458, the supply lines 464 and 474, the diodes 466 and 467, the transistor 485, and the signal line 480 collectively form a three-wire circuit (three-wire connection) 490D.

The first switch 456 (connected to supply line 464) and the second switch 458 (connected to supply line 474) are each selectably and alternatively connectable to a power source (power) 482 and a ground 484 in sound processor. More specifically, while first switch 456 is connected to the power source 482 (i.e., connecting supply line 464 to power), the second switch 458 is connected to the ground 484 (i.e., connecting supply line 474 to ground). This arrangement of the switches 456 and 458 is referred to herein as a first configuration of the three-wire circuit 490D and results in the powering of the first sound input element 461. Conversely, while first switch 456 is connected to the ground 484 (i.e., connecting supply line 464 to ground), the second switch 458 is connected to the power source 484 (i.e., connecting supply line 474 to power). This arrangement of the switches 456 and 458 is referred to herein as a second configuration of the three-wire circuit 490D and results in the activation of the second sound input element 465.

In summary, in the embodiment of FIG. 4D the first sound input element 461 and the second input element 465 are alternatively operable, depending on the configuration of the shared three-wire connection 490D. In other words, the shared three-wire circuit 490D is configured to selectably enable one or the other of the first and second sound input elements for operation with the connected sound processing components 454.

FIGS. 4A-4D illustrate two power sources 482 and two grounds 484 (i.e., one power source and one ground associated with each of the switches 456 and 458). It is to be appreciated that the use of two power sources 482 and the two grounds 484 in FIGS. 4A-4D is merely for purposes of illustration and that the powers sources 482 and grounds 484 may comprise a single power source 482 and a single ground 484, respectively.

Telecoils comprise a series of coils (loops) of wire disposed around an elongate core and are used in an auditory prosthesis to detect electromagnetic signals. More specifically, certain audio sources include, or operate in conjunction with, an audio induction loop that generates an electromagnetic field that varies with an audio signal. Telecoils are designed to detect the varying electromagnetic fields generated by an audio induction loop and generate a corresponding electrical signal, thereby effectively enabling the audio source to be connected to the auditory prosthesis. Audio induction loops can be found, for example, in telephones, or may comprise a neck loop (i.e., a coil of wire worn around a recipient's neck), a room loop (i.e., a large wire loop that sits in floor of a room such as a movie theater, church hall, or living room), etc.

Certain telecoils, sometimes referred to as passive telecoils, are two-wire devices. Other telecoils, sometimes referred to as active telecoils, include an amplifier therein. As such, active telecoils are three wire devices (i.e., ground, power, and signal/output). Embodiments are generally described herein with reference to active (three wire) telecoils. However, certain embodiments may also use passive telecoils.

The wire coils of a telecoil are co-axial with one another and disposed around an elongate core (e.g., ferrite). That is, a telecoil has a central axis that extends through the middle of the wire coils. Similarly, audio induction loops may comprise one or more wire loops that are also disposed around a central axis. In general, telecoils are most effective at detecting a magnetic field generated by an audio induction loop when the wire coils of the telecoil are substantially parallel with the coil(s) forming the audio induction loop (i.e., when the central axis of the telecoil is substantially parallel to the central axis of the audio induction loop).

In most conventional arrangements, a telecoil is incorporated into the external sound processor of an auditory prosthesis. However, telecoils generally have a physical size that makes them one of the largest components in the sound processor. There is also a desire for sound processors to be as small and unobtrusive as possible. As such, due to these size constraints, conventional arrangements use a single telecoil within the sound processor.

To enable a telecoil for use with a telephone, the telecoil is positioned in the sound processor such that, when the sound processor is worn by a recipient, the central axis of the telecoil is substantially horizontal. Alternatively, to enable a telecoil for use with a room/neck loop, the telecoil is positioned in the sound processor such that, when the sound processor is worn by the recipient, the central axis of the telecoil is substantially vertical. As such, the use of a single telecoil in a sound processor has the negative affect that the sound processor may be configured for use with a telephone or configured for use with a room/neck loop, but not both. As such, in conventional arrangements, the designers of a sound processor are forced to pre-determine if the sound processor should be used with a telephone or with a room/neck loop, and then accordingly fix the telecoil within the sound processor in the corresponding orientation (i.e., select one of a horizontal or vertical orientation for the telecoil).

As noted above, presented herein are sound processor accessories that may include a plurality of sound input elements. FIG. 5 illustrates one specific embodiment in which a sound processor accessory 528 comprises two telecoils, shown in FIG. 5 as a first telecoil 560 and a second telecoil 562. In the embodiment of FIG. 5, the sound processor accessory 528 comprises an ear hook 542 and an ear hook extension 544. The ear hook extension 544 comprises a shaft 546 and an in-the-canal component 550. The telecoils 560 and 562 are configured to be electrically connected to sound processing components in the sound processor 126 via a three-wire circuit, as described above. For ease of illustration, the three-wire circuit has been omitted from FIG. 5.

As shown, the telecoils 560 and 562 are disposed in the near-the-canal component 550. The first telecoil 560 has a central axis 591 that, when the sound processor 126 and sound processor 528 are worn by the recipient, is substantially horizontal. Conversely, the second telecoil 562 has a central axis 593 that, when the sound processor 126 and sound processor 528 are worn by the recipient, is substantially vertical. That is, the central axis 591 and 593 are substantially orthogonal to one another.

The embodiment of FIG. 5 has an advantage that the first telecoil 560 is orientated so as to detect magnetic fields generated by a telephone audio induction loop 584, while the second telecoil 562 is orientated so as to detect magnetic fields generated by a room/neck loop 586. As such, there no longer is a need for a system designer to pre-determine which of telephone or room/neck loop is desired. Additionally, because the telecoils 560 and 562 are disposed in the sound processor accessory 528, there is no longer a need for a telecoil in the sound processor 126 and the size of the sound processor may be decreased. Furthermore, telecoils are sensitive circuit elements that, when positioned in a sound processor, may be interfered with by the other circuitry in the sound processor. This interference is reduced and/or substantially eliminated by physically separating the telecoils 560 and 562 from the sound processor 126. Finally, a telecoil for phone operation that is disposed in or adjacent to the ear canal allows for the use of a more natural phone position by the recipient because the speaker in the phone needs to align with the telecoil near the ear canal, rather than a telecoil positioned behind the recipient's ear.

As noted, telecoil 560 is configured to receive signals from a telephone audio induction loop 584, while the telecoil 562 is configured to receive signals from a room/neck loop. As such, because the telecoils 560 and 562 are configured for different uses, only one of the telecoils is generally active at a time. In accordance with embodiments presented herein, a polling process may be executed to switch between the telecoils 560 and 562. In one example polling process, the telecoils 560 and 562 are each briefly activated to see if either one detects a strong signal. The telecoil that detects the strongest signal is activated for use. It is to be appreciated that other methods for selecting which telecoil to use (e.g., manual selection, etc.) may be employed in embodiments presented herein.

Figure 6:
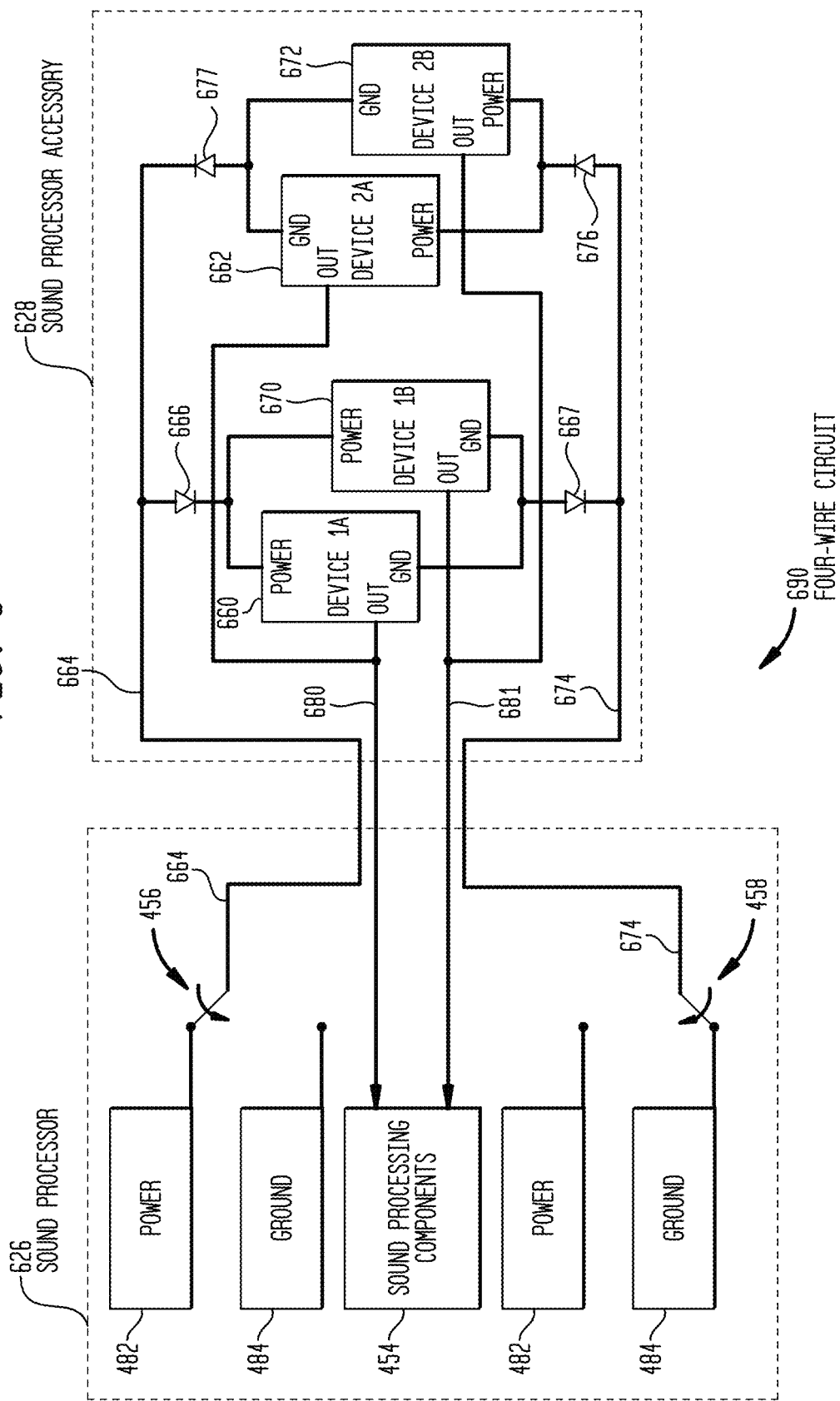
FIG. 6 is a schematic circuit diagram of a sound processor and sound processor accessory in accordance with embodiments presented herein.

The above embodiments primarily illustrate configurations that include two sound input elements in a sound processor accessory. It is to be appreciated that embodiments presented herein are not limited to sound input elements, but rather may include any other two or three wire device. It is also to be appreciated that embodiments presented herein are not limited to the use of two sound input elements or devices within a sound processor accessory. For example, FIG. 6 illustrates an embodiment where four devices 660, 662, 670, and 672 are disposed in a sound processor accessory 628. The devices 660, 662, 670, and 672 may comprise any three-wire device. However, for ease of reference, FIG. 6 will be described with reference to devices 660, 662, 670, and 672 as sound input elements.

In the embodiment of FIG. 6, the sound processor accessory 628 is mechanically and electrically connected to a sound processor 626. The sound processor 626 is similar to the sound processor 126 described above with reference to FIGS. 4A-4D and comprises a power source 482, a ground 484, a first switch 456, a second switch 458, and sound processing components 454. Sound processor accessory 628 comprises a first sound input element 660 (device 1A), a second sound input element 670 (device 1B), a third sound input element 662 (device 2A), and a fourth sound input element 672 (device 2B). The sound processor accessory 628 may be an ear hook (such as shown in FIG. 2) or an ear hook with an ear hook extension that includes, for example, a near-the-canal, in-the-canal, etc. component (such as shown in FIG. 3).

The sound input elements 660, 670, 662, and 672 are all three-wire devices. That is, each of the sound input elements 660, 670, 662, and 672 include a GND terminal, a POWER terminal, and a signal connection or output terminal.

The first switch 456 is connected to a supply line 664 that extends to a diode 666 that is connected to the POWER terminals of both of the sound input elements 660 and 670. The diodes 666 and 667 have anode and cathode connections such that the power terminals of the sound input elements 660 and 670 are effectively connected to the supply line 664 when the supply line 664 is at a higher potential than supply 674 (i.e., supply line 664 is connected to power 482 and supply line 674 is connected to ground 484). Similarly, the power terminals of the sound input elements 660 and 670 are largely disconnected from supply line 664 when diode 666 is reverse biased by having supply line 664 at a lower potential than supply line 674 (i.e., supply line 664 is connected to ground 484 and supply line 674 is connected to power 482).

The second switch 458 is connected to a supply line 674 that extends to a diode 676 that is connected to the POWER terminals of both of the third and fourth sound input elements 662 and 672. Similarly, the diodes 676 and 677 have anode and cathode connections such that the power terminals of the sound input elements 662 and 672 are effectively connected to the supply line 674 when the supply line 674 is at a higher potential than supply 664 (i.e., supply line 674 is connected to power 482 and supply line 664 is connected to ground 484). Similarly, the power terminals of the sound input elements 662 and 672 are largely disconnected from supply line 674 when diode 676 is reverse biased by having supply line 674 at a lower potential than supply line 664 (i.e., supply line 674 is connected to ground 484 and supply line 664 is connected to power 482).

The output terminals of both the first sound input element 660 and the third sound input element 662 are connected to a signal line 680. The output terminals of both the second sound input element 670 and the fourth sound input element 672 are connected to a signal line 681. The signal lines 680 and 681 are also connected to the sound processing components 454 in the sound processor 626. The switches 456 and 458, the supply lines 664 and 674, the diodes 666, 677, 667, and 676, and the signal lines 680 and 681 collectively form a four-wire circuit (four-wire connection) 690.

The first switch 456 (connected to supply line 664) and the second switch 458 (connected to supply line 674) are each selectably and alternatively connectable to a power source (power) 482 and a ground 484 in the sound processor 626. More specifically, while first switch 456 is connected to the power source 482 (i.e., connecting signal 464 to power), the second switch 458 is connected to the ground 484 (i.e., connecting supply line 474 to ground). This arrangement of the switches 456 and 458 is referred to herein as a first configuration of the four-wire circuit 690 and results in the powering of the first and second sound input elements 660 and 670. Conversely, while first switch 456 is connected to the ground 484 (i.e., connecting supply line 464 to ground), the second switch 458 is connected to the power source 484 (i.e., connecting supply line 474 to power). This arrangement of the switches 456 and 458 is referred to herein as a second configuration of the four-wire connection 690 and results in the powering of the third and fourth sound input elements 662 and 672.

In summary, in the embodiment of FIG. 6, the sound processor accessory 628 comprises two sets of one or more devices (i.e., a first set comprising sound input elements 660 and 670 and a second set comprising sound input elements 662 and 672). The four-wire circuit 690 connects both of the first and second sets of one or more devices to sound processing components such that the first and second sets of one or more devices are alternatively operable (i.e., either devices 1A and 1B are active or devices 2A and 2B are active). In other words, the four-wire circuit 690 is configured to selectably enable one or the other of the first and second sets of sound input elements for operation with the connected sound processing components 454.

As noted, FIG. 6 illustrates two sets of devices that each comprises two devices, wherein the two sets are alternatively operable. In alternative embodiments, a four-wire circuit may be provided to connect only two devices to the sound processing components 454. For example, the embodiment of FIG. 6 may be modified to eliminate the third and fourth sound input elements 662 and 672, leaving only the first and second sound input elements 660 and 670. In such an embodiment, the first and second sound input elements 660 and 670 would be continuously active.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An apparatus, comprising:
   a first three-wire device;
   a second three-wire device; and
   a three-wire connection configured to selectably enable one or the other of the first and second three-wire devices for operation with connected sound processing components of a sound processor, wherein the three-wire connection includes:
      a signal line connected to both of the first and second three-wire devices,
      a first wire connected to a power supply input of the first three-wire device via a diode, connected to a ground of the second three-wire device, and selectably connectable to one of a power supply and a ground of the sound processor via a switch, and
      a second wire connected to a power supply input of the second three-wire device via a diode, connected to a ground of the first three-wire device, and selectably connectable to one of the power supply and the ground of the sound processor via a switch.

2. The apparatus of claim 1, further comprising:
   a diode connecting the ground of the first three-wire device to the second wire.

3. The apparatus of claim 2, further comprising:
   a diode connecting the ground of the second three-wire device to the first wire.

4. The apparatus of claim 1, further comprising a housing forming an ear hook, and wherein the three-wire circuit is configured to electrically connect the first and second three-wire devices to sound processing components of a behind-the-ear sound processor.

5. The apparatus of claim 4, wherein the first and second three-wire devices are disposed in the housing.

6. The apparatus of claim 4, further comprising an elongate extension having a distal end in which the first and second three-wire devices are disposed.

7. An apparatus, comprising:
   a first set of one or more devices including first and second devices;
   a second set of one or more devices including third and fourth devices; and
   a circuit connecting both of the first and second sets of one or more devices to components of a sound processor such that the first and second sets of one or more devices are alternatively operable, wherein the circuit comprises:
      a first wire connected to power supply inputs of the first and second devices via a diode, connected to a ground of the third and fourth devices via a diode, and selectably connectable to one of a power supply and a ground of the sound processor via a switch, and
      a second wire connected to power supply inputs of the third and fourth devices via a diode, connected to a ground of the first and second devices via a diode, and selectably connectable to one of the power supply and the ground of the sound processor via a switch.

8. The apparatus of claim 7, wherein the first and second wires are supply lines each selectably connectable to one of a power supply and a ground of the sound processor; and wherein the circuit further comprises:
   two or more signal lines.

9. The apparatus of claim 7, wherein further comprising a housing forming an ear hook, and wherein the circuit is configured to electrically connect the first and second sets of one or more devices to components of a behind-the-ear sound processor.

10. The apparatus of claim 9, wherein the first and second sets of one or more devices are disposed in the housing.

11. The apparatus of claim 9, further comprising an elongate extension having a distal end in which the first and second sets of one or more devices are disposed.

12. An auditory prosthesis, comprising:
   a sound processor;
   a separate sound processor accessory connected to the sound processor and comprising at least first and second telecoils; and
   a circuit configured to selectably enable one or the other of the first and second telecoils for operation with the sound processor, wherein the circuit includes:
      a first wire connected to a power supply input of the first telecoil via a diode, connected to a ground of the second telecoil, and selectably connectable to one of a power supply and a ground of the sound processor via a switch, and
      a second wire connected to a power supply input of the second telecoil via a diode, connected to a ground of the first telecoil, and selectably connectable to one of the power supply and the ground of the sound processor via a switch.

13. The auditory prosthesis of claim 12, wherein the sound processor comprises a behind-the-ear sound processor.

14. The auditory prosthesis of claim 13, wherein the sound processor accessory comprises a housing forming an ear hook and wherein the one or more telecoils are disposed in the housing.

15. The auditory prosthesis of claim 13, wherein the sound processor accessory comprises an elongate extension having a distal end in which the one or more telecoils are disposed.

16. The auditory prosthesis of claim 12, wherein the first and second telecoils are oriented such that coils of the first telecoil are substantially orthogonal to coils of the second telecoil.

17. The apparatus of claim 1, wherein the first three-wire device and the second three-wire device are each sound input elements.

18. The apparatus of claim 17, wherein the first sound input element comprises a telecoil, and wherein the second sound input element comprises a microphone.

19. The apparatus of claim 17, wherein the first sound input element comprises a first microphone, and wherein the second sound input element comprises a second microphone.

20. The apparatus of claim 7, wherein the first set of one or more devices and the second set of one or more devices each comprise one or more sound input elements.

21. The apparatus of claim 17, wherein the first sound input element comprises a first telecoil, and wherein the second sound input element comprises a second telecoil.

22. The apparatus of claim 21, wherein the first and second telecoils are orientated such that coils of the first telecoil are substantially orthogonal to coils of the second telecoil.

23. The apparatus of claim 17, wherein at least one of the sound input elements comprises an audio input connector configured to receive signals from an external audio device.

24. An auditory prosthesis, comprising:

a sound processor;

a separate sound processor accessory connected to the sound processor and comprising at least first and second devices; and a circuit configured to selectably enable one or the other of the first and devices for operation with the sound processor, wherein the circuit includes:

a signal line connected to both of the first and second devices, a first wire connected to a power supply input of the first device via a diode, connected to a ground of the second device, and selectably connectable to one of a power supply and a ground of the sound processor via a switch, and a second wire connected to: a ground of the first device via a diode, connected to a ground of the second device, and selectably connectable to one of the power supply and the ground of the sound processor via a switch.

25. The auditory prosthesis of claim 24, wherein the second device is a two-terminal self-powered device, and wherein the first and second wires are each connected to the ground of the second device via transistor.

26. The auditory prosthesis of claim 25, wherein the two-terminal self-powered device is an audio input port.

27. The auditory prosthesis of claim 24, wherein the first device is a microphone.

* * * * *